United States Patent
Paufique

(10) Patent No.: US 11,065,194 B2
(45) Date of Patent: Jul. 20, 2021

(54) **COSMETIC USE OF EXTRACTS OF *SALVIA MILTIORRHIZA* ROOTS, SPECIAL EXTRACTS OF *SALVIA MILTIORRHIZA* ROOTS AND COSMETIC COMPOSITIONS CONTAINING SUCH EXTRACTS**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 16/239,769

(22) Filed: Jan. 4, 2019

(65) Prior Publication Data

US 2019/0209457 A1 Jul. 11, 2019

(30) Foreign Application Priority Data

Jan. 5, 2018 (FR) .............................. FR 18 00012

(51) Int. Cl.
- *A61K 36/537* (2006.01)
- *A61K 8/9789* (2017.01)
- *A61Q 19/00* (2006.01)
- *A61P 17/04* (2006.01)

(52) U.S. Cl.
CPC .......... *A61K 8/9789* (2017.08); *A61K 36/537* (2013.01); *A61P 17/04* (2018.01); *A61Q 19/00* (2013.01); *A61Q 19/005* (2013.01); *A61K 2236/333* (2013.01); *A61K 2800/75* (2013.01)

(58) Field of Classification Search
None
See application file for complete search history.

(56) References Cited

U.S. PATENT DOCUMENTS

| 9,283,256 B2 * | 3/2016 | Zhong ................. A61K 36/537 |
| 2003/0091665 A1 * | 5/2003 | Lu .......................... A61K 36/03 |
| | | 424/761 |

FOREIGN PATENT DOCUMENTS

| CN | 102580054 A | 7/2012 |
| CN | 105267175 A | 1/2016 |
| CN | 106177408 A | 12/2017 |

OTHER PUBLICATIONS

Wang (2010) Journal of Medicinal Plants Research, vol. 4(25): 2813-2820. (Year: 2010).*
Tan et al. (2014) BMC Biotechnology 14: 74 (10 pages) (Year: 2014).*
Zhou et al. (2005) Journal of Clinical Pharmacology 45: 1345-1359. (Year: 2005).*
Sun Y. et al., "Isolation and purification of salvianolic acid A and salvianolic acid B from salvia miltriorrhiza by high-speed counter-current chromatography and comparison of their antioxidant activity", Journal of Chromatography B, 2009, pp. 733-737, 877.
Chen J., et al., "Separation and identification of water-soluble salvianolic acids from Salvia miltiorrhiza Bunge by high-speed counter-current chromatography and ESI-MS analysis", Elsevier, Talanta 69, 2006, pp. 172-179.
Lee S., "Anti-inflammatory effects of Salviae Miltiorrhizae Radix extract on RAW264.7 cell. via anti-oxidative activities", The Korean Association of Herbology, 2014, pp. 89-94, vol. 30(4).

* cited by examiner

*Primary Examiner* — Russell G Fiebig
(74) *Attorney, Agent, or Firm* — Greer, Burns & Crain, Ltd.

(57) ABSTRACT

Methods in which an extract of *Salvia miltiorrhiza* roots is applied to the skin for a soothing cosmetic topical treatment. The invention also concerns a particular extract of *Salvia miltiorrhiza* roots, as well as compositions containing this extract and a cosmetic treatment method providing a soothing effect to the skin.

8 Claims, 4 Drawing Sheets

COSMETIC USE OF EXTRACTS OF *SALVIA MILTIORRHIZA* ROOTS, SPECIAL EXTRACTS OF *SALVIA MILTIORRHIZA* ROOTS AND COSMETIC COMPOSITIONS CONTAINING SUCH EXTRACTS

CROSS-REFERENCE TO RELATED APPLICATIONS

This application claims priority to French patent application FR 18 00012 filed Jan. 1, 2018, the entire disclosure of which is incorporated herein by reference.

TECHNICAL FIELD

The invention concerns the cosmetic treatment of skins aggressed by external stimuli such as cold, pollution and chemical stresses. The invention relates in particular to a natural extract produced by plants, to the cosmetic compositions that contain it and to its cosmetic use as a topical application to soothe aggressed skins.

BACKGROUND

The syndrome of sensitive skin has become considerably more widespread over the last twenty years. In fact, today, an increasing number of people have sensitive or intolerant skin.

Skin sensitivity is a common disorder, the symptoms of which are stinging, overheating, tightness and/or redness that have considerable psychological consequences. Different parameters contribute to the triggering of these symptoms:
  On the one hand, genetic factors, connected with gender or ethnicity: women are affected more than men due to a thinner epidermis and hormonal changes; Asian skins are more susceptible to aggressions than Caucasian or Afro-American skins.
  On the other hand, lifestyle: sensitive skin reacts abnormally to aggressions of different types:
    Environmental (UV, heat, cold, pollution)
    Chemical (detergents, hard water)
    Physiological (stress, hormones)
    Physical (clothing, shaving, epilation).
From a biological point of view, sensitive or intolerant skins have a dysfunction of three biological components:
  a neuronal hyperactivity, namely an excessive response of the nerve endings, specifically a hyperstimulation of nociceptors including TRPV1, which is the reference receptor,
  an impaired barrier function, specifically a change in the lipid composition and behavior of the keratinocytes, and
  an exacerbated inflammation, specifically an excess production of pro-inflammatory substances.

Amongst the environmental factors, cold and pollution figure among the major stresses that have the greatest impact on sensitive skins. In fact, they upset the skin balance by acting directly on the three biological components of sensitive skins, thus increasing the unpleasant sensations on the skin.

Currently, the cosmetic treatments available for soothing sensitive skins focus mainly on problems of the skin's sensitivity to chemical aggressions, without taking into account the environment, lifestyle or ethnicity of the persons concerned, which results in their action being unsatisfactory. Furthermore, they do not act on all three biological components of sensitive skins.

SUMMARY

The aim of the invention is to propose a solution that overcomes these drawbacks, specifically a solution of natural origin that has a transversal action on the three biological components involved in skin sensitivity, and that has a "multi-ethnic" soothing effect suited to the lifestyle and environment of the persons concerned.

To this end, the subject-matter of the invention concerns the use of an extract of *Salvia miltiorrhiza* roots for a soothing cosmetic topical treatment of the skin.

*Salvia miltiorrhiza*, or red sage, is also known by the name of Danshen. It is a medicinal plant grown in China, but it is also found very commonly in the wild. With a high resistance to abiotic stress, it adapts to any change in environment. In fact, the majority of *Salvia miltiorrhiza* crops are located in the regions of Sichuan and Shandong where the winters are harsh with low temperatures. Grown for its therapeutic effects both on the body and the mind, the dried root of *Salvia miltiorrhiza* plays a vital role in Chinese pharmacopoeia because it is a real concentrate of so-called "good health" molecules. Used traditionally for thousands of years, the root of red sage is still widely used in the practice of modern-day medicine. Among the properties described in traditional Chinese medicine, Danshen is said to be capable of improving blood circulation and treating cardiovascular, brain and liver diseases or even some skin diseases.

The invention covers the use of an extract of Danshen in cosmetics for a specific soothing effect, and not of Danshen as envisaged in the Chinese or Japanese pharmacopeia.
  Advantageously, this extract:
  is obtained by implementing a method of extraction using solvents of plant origin,
  has an action on the three biological components involved in skin sensitivity:
    reduction of neuronal hyperactivity, specifically inactivation of the TRPV1 receptor,
    beneficial effect on the barrier function and improvement of the skin barrier,
    reduction of inflammation,
  has a soothing effect on the skin, with an efficacy on Caucasian or Asian skins subject to hypersensitivity,
  constitutes a global solution adapted to the lifestyle and environment of the persons concerned and having a soothing action on skin subjected to cold or pollution.

Thus, the use of an extract of *Salvia miltiorrhiza* according to the invention soothes the skin and comforts and protects delicate skin, particularly on the face and hands. The invention also advantageously lastingly nourishes and moisturizes skin, makes it softer and more resistant to external aggressions, and reduces redness of the skin, making it less sensitive, less irritable and less uncomfortable.

The invention also concerns a specific extract of *Salvia miltiorrhiza* roots comprising at least 5% by weight of phenolic acids in relation to the total weight of dry matter of the extract, as well as cosmetic compositions containing such an extract.

The subject-matter of the invention also includes a non-therapeutic method of cosmetic treatment of the skin having a soothing effect consisting in the topical application onto the skin of a composition comprising an extract of *Salvia miltiorrhiza* roots.

Further features and advantages of the invention will emerge from the following detailed description of the invention with reference to the Figures.

DEFINITIONS

Figure 1:
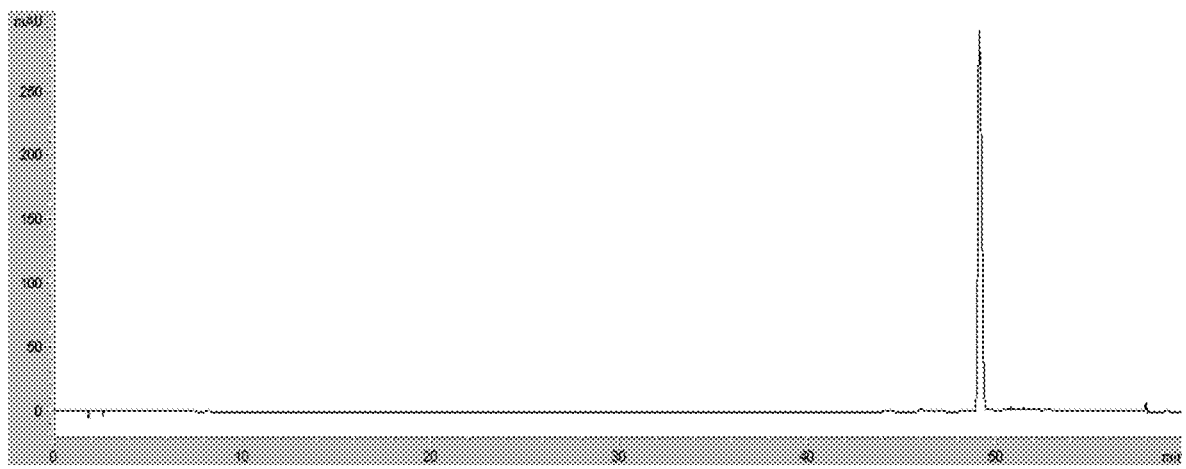
FIG. 1: the HPLC chromatogram of standard Cryptotanshinone 0.25 g/L.

"Cosmetic agent," as defined by the invention, means equally a cosmetic active ingredient or a cosmetic active agent, i.e. at least one molecule, preferably an assembly of several molecules, having an effect on skin cells.

"Containing an 'X' or "comprising an 'X'," unless stated otherwise, as defined by the invention, means that which contains or comprises at least one "X." "X" is quantifiable according to an analytical method chosen on the basis of "X" and the knowledge of a person skilled in the art.

"Extract" of *Salvia miltiorrhiza* roots, as defined by the invention, means any molecule or mixture of molecules obtained from *Salvia miltiorrhiza* roots. There may be one or more native molecules or one or more molecules obtained by any type of extraction and transformation of native molecules of *Salvia miltiorrhiza* roots.

"Sensitive skin" or "intolerant skin," as defined by the invention, means a skin with a reduced tolerance threshold as regards tingling, overheating, tightness, redness, etc.

DETAILED DESCRIPTION

The subject-matter of the invention thus relates to the use of an extract of *Salvia miltiorrhiza* roots for a cosmetic topical treatment that soothes the skin. Cosmetic treatment means a non-therapeutic cosmetic treatment.

In fact, according to the invention, an extract of *Salvia miltiorrhiza* roots when it is applied to the skin, particularly a sensitive skin, is capable of soothing and, specifically, of:
neutralizing the neuronal hyperactivity of the skin, and/or
preserving the barrier function of the skin, and/or
limiting the inflammation of the skin.

Preferably, the invention aims to use an extract of *Salvia miltiorrhiza* roots in order to act on these three factors at the same time.

Neuronal hyperactivity is an excessive response of the nerve endings of the skin linked to a hyperactivation of the nociceptors. In fact, the skin hosts a network of nerve fibers involved in sensoriality, i.e. the perception of sensations of pain, itching and thermo-sensations. This function is assured by a family of receptors called TRP (Transient Receptor Potential). Within this family, TRPV1 (Transient Receptor Potential Vanilloid 1) plays a crucial role. In fact, this receptor is transversal; it can be activated by a wide variety of exogenous and endogenous stimuli, including certain natural agonists such as capsaicin. Recent studies suggest that skin hypersensitive reactions are closely linked to the innervation of the epidermis and the hyper activation of TRPV1. Furthermore, the latter is now considered to be the reference marker for sensitive skins (Duarte et al., 2017; Gouin et al., 2017).

In terms of sensitive neurons, its activation leads to influxes of calcium and the release of neuromediators responsible for a neurogenic inflammation of the skin (Boillat et al., 2014; Gouin et al., 2017). Also expressed by other cell types such as keratinocytes, the activation of TRPV1 causes their apoptosis as well as the synthesis and secretion of pro-inflammatory substances. These phenomena thus limit the establishment of a functional barrier function (Tóth et al., 2014; Misery et al., 2016).

TRPV1 therefore plays a central role in skin sensitivity. Its activation is responsible for the appearance of a collection of unpleasant skin sensations such as pain, itching, overheating and stinging (Misery et al., 2016; Duarte et al., 2017). Its inactivation therefore constitutes a prerequisite for the development of a soothing active ingredient.

According to the invention, the use of an extract of *Salvia miltiorrhiza* roots on the skin, particularly on a sensitive skin, inhibits the activation of the receptor of sensitive skins TRPV1 and thus limits the neuronal hyperactivity of the skin and the skin manifestations resulting therefrom, such as stinging.

In addition to neuronal hyperactivity, numerous studies suggest that skin sensitivity is linked to an impairment of the barrier function. This alteration causes a feeling of discomfort (Misery et al., 2016). Sensitive skins have demonstrated:
a loss of the protective hydrolipidic film;
an alteration in the organization of the lipidic composition of the stratum corneum;
poor corneocyte adhesion (Draelos, 1997; Tóth et al., 2014; Misery et al., 2016; Richters et al., 2017).

To this is added the apoptosis of the keratinocytes caused by the influx of calcium generated by the activation of TRPV1 (Tóth et al., 2014).

Damage of the skin barrier leads to:
an increase in transepidermal water loss, explaining the dryness felt by those subject to skin hypersensitivity (Saint-Martory et al., 2008; Pinto et al., 2011; Duarte et al., 2017; Richters et al., 2017);
increased exposure of sensitive neurons and consequently exacerbated sensory perceptions (Richters et al., 2015);
easier penetration of irritant and allergenic substances that are the source of an inflammation characterized by the production of cytokines, leukotrienes and prostaglandins (Draelos, 1997; Misery et al., 2016; Duarte et al., 2017).

In sensitive skins, the impairment of the barrier function leads to dehydration that contributes to the appearance of sensations of tightness, irritation and discomfort. Preserving the barrier function therefore constitutes an important element that influences the comfort given by a treatment.

According to the invention, the use of an extract of *Salvia miltiorrhiza* roots on the skin, particularly on sensitive skin, significantly reduces transepidermal water loss and significantly boosts the hydration of the skin, specifically on the face and hands.

The neuronal hyperactivity and impairment of the barrier function lead to the triggering of pro-inflammatory processes:

- with respect to sensitive neurons, neuromediators secreted in response to the simulation of TRPV1 activate the keratinocytes located near the nerve endings (Tóth et al., 2014; Misery et al., 2016; Gouin et al., 2017). By attaching to their specific receptors, they cause the synthesis of pro-inflammatory substances such as cyclooxygenase 2 (COX-2), prostaglandin E2 (PGE2) and leukotrienes B4 (LTB4);
- as a result of the impairment of the barrier function, the penetration of irritant and allergenic substances causes an inflammation characterized by the production of cytokines, prostaglandins and leukotrienes (Duarte et al., 2017).

The production of the inflammatory cocktail causes:

- the recruitment of inflammatory cells reinforcing the extent and chronicity of the inflammation (Tóth et al., 2014; Misery et al., 2016; Gouin et al., 2017);
- the indirect activation of TRPV1, thus sustaining neuronal hyperactivity (Gouin et al., 2017);
- functional changes in the skin barrier (Vestergaard et al., 2012).

In sensitive skins, chronic inflammation leads to itching and redness. Controlling the inflammatory phenomenon thus represents an important action for soothing sensitive skins.

According to the invention, the use of an extract of *Salvia miltiorrhiza* roots on the skin, particularly on sensitive skin, significantly inhibits the secretion of PGE2 and the synthesis of COX in aggressed skins. An extract of *Salvia miltiorrhiza* roots can consequently limit the inflammatory response of the skin faced with an aggression, and thus reduce cutaneous redness in aggressed skins.

The use of an extract of *Salvia miltiorrhiza* roots on the skin thus improves neuronal reactivity, the barrier function and the inflammatory state of the skin, and consequently helps sensitive skins in their struggle against the stimuli of day-to-day life. Skin comfort is improved, tightening and redness are reduced, and the skin is soothed, softer, more moisturized and more resistant to external aggressions. The use of an extract of *Salvia miltiorrhiza* roots on the skin makes the skin less sensitive, less irritable, less uncomfortable and lastingly moisturized.

The invention therefore specifically has as its subject-matter the cosmetic use of an extract of *Salvia miltiorrhiza* roots in a cosmetic composition as a cosmetic agent, in particular as a cosmetic agent designed to soothe the skin, specifically in order to:

- neutralize the neuronal hyperactivity of the skin, and/or
- preserve the barrier function of the skin, and/or
- limit the inflammation of the skin, and specifically, to reduce cutaneous hypersensitive reactions and/or reduce the sensations of tightening of the skin.

The invention envisages a use on all skin types, particularly for sensitive skins and even more particularly for skins having undergone an aggression that is:

- environmental (UV, heat, cold, pollution), and/or
- chemical (detergents, hard water) and/or
- physiological (stress, hormones) and/or
- physical (clothing, shaving, epilation).

Preferably, the invention envisages the use of an extract of *Salvia miltiorrhiza* roots for a soothing non-therapeutic cosmetic topical treatment of skins aggressed by cold and/or pollution and/or chemical stresses.

The extract of *Salvia miltiorrhiza* roots advantageously acts indiscriminately on Caucasian and Asian skins.

The useful extracts of *Salvia miltiorrhiza* roots according to the invention can be of any type.

Preferably, an extract of *Salvia miltiorrhiza* roots is used that comprises at least 5% by weight of total polyphenols in relation to the total weight of dry matter of the extract, preferably a content of between 5 and 15% of total polyphenols in relation to the total weight of dry matter of the extract.

The total polyphenols content can be measured for example by colorimetric assay. Even more preferentially, an extract is used that comprises at least 70% polyphenols of the salvianolic acid type by weight in relation to the total weight of the total polyphenols present in the extract. Salvianolic acids are a family of phenolic acids consisting of several molecules. They include salvianolic acid A, salvianolic acid B, salvianolic acid C, methylsalvianolic acid C, isosalvianolic acid C, salvianolic acid C, salvianolic acid E, salvianolic acid F, salvianolic acid I, and salvianolic acid J. The term "salvianolic acids" or "salvianolic acid type" therefore means at least one of these salvianolic acids.

Preferably, salvianolic acid type acids represent at least 3.5% by weight of dry matter of the extract.

The characterization of phenolic acids present in the extract is achieved for example by liquid chromatography combined with mass spectrometry.

The total polyphenols and in particular the phenolic acid type salvianolic acids play an active role in the efficacy of the extract for soothing the skin and in particular have an important action on the secretion of PGE2.

Preferably, the extract of *Salvia miltiorrhiza* roots according to the invention does not contain cryptotanshinone, unlike the root of the plant, which does contain it. This molecule presents a danger due to the risk of cardiotoxicity and developmental malformation.

The method of identifying cryptotanshinone used to prove its absence in the extract according to the invention is either that described in the Japanese pharmacopeia for identifying the *Salvia miltiorrhiza* root, or liquid chromatography with UV detection.

According to a particularly suitable embodiment, the extract according to the invention, in addition to polyphenols, contains:

- sugars, and/or
- proteins, and/or
- minerals.

The sugar content in the extract can be determined by the DUBOIS method (Dubois M. et al., *Analytical chemistry*, 28, 3, 350-356, 1956).

The extracts according to the invention therefore comprise a large quantity of carbohydrates. Preferably, the sugar content of the extract according to the invention is at least 75% by weight of dry matter of the extract.

Preferably, the carbohydrates of the extract have the following characteristics:

- the carbohydrates contained in the extract are sugars with a molar mass of less than 1,260 Da, and/or
- at least 60% of the carbohydrates are oligosaccharides and polysaccharides with molar masses of between 180 and 1,260 Da (degree of polymerization between 1 and 7), the percentage being given by weight in relation to the total weight of the carbohydrates of the extract, less than 40% of the carbohydrates are monosaccharides, the percentage being given by weight in relation to the total weight of the carbohydrates of the extract.

The simple sugars constituting the carbohydrates of the extract according to the invention are preferentially galactose, fructose and glucose.

As regards the proteins, the extracts according to the invention preferably have a protein content of less than 5% by weight in relation to the total weight of dry matter of the extract.

The protein content is preferably determined by the KJELDHAL method (reference: Official method of analysis of the A.O.C., 12th ed. W Horwitz, E. D., New-York, 15-60, 1975).

As regards the minerals, the extracts according to the invention preferably have a mineral ash content of less than 8% by weight in relation to the total weight of dry matter of the extract.

The crude ash content can be determined by weighing the residues resulting from incineration of the samples of the extract at 550° C. in an electric-muffle furnace.

A particularly suitable extract of Salvia miltiorrhiza roots is an extract obtained using a solvent of natural origin, in particular a solvent of plant origin such as a mixture of water/butylene glycol of plant origin.

The extract according to the invention can be in solid form or liquid form, preferably in liquid form.

If it is in liquid form, it is preferably in the form of a clear yellow liquid.

The extract according to the invention can be obtained by any method that enables an extract of Salvia miltiorrhiza root having the claimed characteristics to be obtained. Preferably this method includes at least one step of solubilization of Salvia miltiorrhiza roots and at least one step of molecular sorting.

The extract of Salvia miltiorrhiza roots according to the invention can in particular be obtained by a method comprising the implementation of the following steps:
  solubilization of the Salvia miltiorrhiza roots between 50 and 500 g/l, in a water/butylene glycol mixture (water/butylene glycol ratio between 30/90 and 5/95, for example 15/18),
  separation of the soluble and insoluble phases, preferably by decantation, filtration or centrifugation,
  recovery of the soluble phase,
  filtration with molecular sorting in order to eliminate molecules with a molar mass exceeding 2000 Da,
  sterilizing filtration.

The extract according to the invention is preferably used as a cosmetic agent in compositions, these compositions comprising a cosmetically acceptable medium. Such compositions are in different galenic forms, suitable for application onto the skin, particularly the skin of the face.

These compositions can in particular be in the form of oil-in-water emulsions, water-in-oil emulsions, multiple emulsions (Water/Oil/Water or Oil/Water/Oil), which may be microemulsions or nanoemulsions, or in the form of solutions, suspensions, hydrodispersions, creams, gels, aqueous gels or powders. They can be more or less fluid and have the appearance of a lotion, shampoo, cream or foam. Preferably, they are creams or gels.

They may be compositions comprising at least 0.25% of an extract of Salvia miltiorrhiza roots according to the invention, preferably between 0.5 and 5%, the percentages being given by weight in relation to the weight of the composition.

These compositions comprise, in addition to the extract of Salvia miltiorrhiza roots, a physiologically acceptable and preferably cosmetically acceptable medium, i.e. that does not cause sensations of unacceptable discomfort for the user such as redness, tightness or stinging.

The compositions according to the invention can contain as an additive at least one compound chosen from:
  oils, which can be chosen specifically from silicone oils, linear or cyclic, volatile or non-volatile;
  waxes, such as ozokerite, polyethylene was, bees wax or carnauba wax,
  silicone elastomers,
  surfactants, preferably emulsifiers, provided that they are non-ionic, anionic, cationic or amphoteric,
  co-surfactants, such as linear fatty alcohols,
  thickeners and/or gelling agents,
  humectants, such as polyols like glycerin,
  dyes, preservatives, loads,
  lifting agents,
  sequestrants,
  perfumes,
  and their mixtures, this list being non-limiting.

Examples of these additives are given specifically in the CTFA Dictionary (International Cosmetic Ingredient Dictionary and Handbook published by the Personal Care Product Council).

Clearly, a person skilled in the art would be sure to choose any complementary compounds, active or non-active, and their quantity, so that the advantageous properties of the mixture are not, or not substantially, altered by the envisaged addition.

These compositions are specifically intended for use on the skin for a soothing effect.

The subject-matter of the invention therefore also relates to a non-therapeutic cosmetic method of treating the skin for a soothing effect, in particular for a soothing effect on sensitive skin, consisting in the topical application onto the skin of a composition comprising an extract according to the invention. The method is particularly suitable for a soothing effect on skins aggressed by the cold and/or pollution and/or by chemical stresses.

In order to illustrate the cosmetic effects of an extract of Salvia miltiorrhiza roots, the following examples with their test results are presented below.

EXAMPLES

Examples of Extracts

Several extracts of the invention have been made by varying the parameters of the method.

The analytical study of the different extracts presented in the examples was conducted as follows:
  The dry matter is determined by weighing 3 g of product added to 10 g of sand placed in an oven at 105° C. for 40 h.
  The pH is measured by the potentiometric method. The measurements are taken at room temperature.
  The total nitrogen is measured according to the KJELDHAL method (Reference: Official method of analysis of the A.O.C., 12th ed. W Horwitz, E. D., New-York, 15-60, 1975). This method enables the protein content to be determined.
  The crude ash content is determined by weighing the residues resulting from the incineration of the samples of extracts according to the invention at 550° C. in an electric-muffle furnace (VULCAN™ 3.550-NDI).

5 grams of the sample are weighed in a pre-calibrated crucible and are placed in the furnace.

The mineralization program comprises a first stage of 3 hours at 110° C. followed by a second stage of 9 hours at 550° C. The temperature of 550° C. is maintained until the ashes are white. The crucible and its contents are then placed immediately in a desiccator until completely cooled and then weighed.

The weight of the residue is calculated by deducting the tare.

The total sugars are determined using the DUBOIS method (Dubois M. et al., *Analytical chemistry*, 28, 3, 350-356, 1956).

All of the functions are released in the presence of concentrated sulfuric acid and give, with phenol, an orange-yellow compound. The color obtained, measured at 490 nm on a spectrophotometer, is proportional to the quantity of total sugars of the sample.

Calibration solutions are prepared from a glucose standard of between 25 and 125 mg/L. A calibration curve of the optical densities of the calibration solutions according to their concentration is constructed.

The samples of the extracts according to the invention are pre-diluted with distilled water, so that the sugar content corresponds to the calibration range.

The quantity of total sugars of the samples is determined thanks to the calibration curve.

The quantification of the polyphenols is achieved by colorimetric assay.

Phenolic compounds form, in the presence of potassium ferrocyanide and iron chloride, colored complexes that can be determined by spectrophotometry at 715 nm. The intensity of this color is proportional to the quantity of phenolic compounds present in the sample.

Calibration solutions are prepared from a hesperidin standard of 40 to 120 mg/L. A calibration curve of the optical densities of the calibration solutions according to their concentration is constructed.

Samples of extracts are pre-diluted with distilled water, so that their polyphenol content corresponds to the calibration range.

The quantity of polyphenols in the samples is determined thanks to the calibration curve.

Example 1 of the Extract According to the Invention

The extract of Example 1 is obtained by implementing the following method:
- dissolve 50 g of powder of dried *Salvia miltiorrhiza* roots in 1 L of a mixture of water/butylene glycol (water/glycol butylene ratio 10/90),
- separate the soluble and insoluble phase by decantation, recover the soluble phase,
- filter with a molecular sieve to exclude the molecules with a molar mass of more than 2,000 Da,
- sterilize through a 0.22µ filter.

The extract of Example 1 is in the form of a clear yellow liquid. The dry matter content is 29.2 g/L.

The chemical composition of the extract of Example 1 is as follows (the percentages being given by weight of dry matter):
Sugars: 25.9 g/L, i.e. 89%
Polyphenols: 2.2 g/L in hesperidin range, i.e. 8%,
Ashes: 2.5%,
Proteins: 0.5%

The phenolic compounds of the extract are distributed as follows:
Hydrophilic phenolic acids: 85%
Other compounds: 15%

The salvianolic acid B content is estimated at 105 ppm.

The absence of cryptotanshinone was determined by liquid chromatography with UV detection, under the following conditions:
Column: Alltech Altima C18 150×4.6 mm diam 3 µm with a pre-column having the same characteristics.
Solvents:
A: ultrapure water with 0.05% formic acid
B: acetonitrile
Gradient:

| Time (minutes) | % A | % B |
| --- | --- | --- |
| 0 | 95 | 5 |
| 45 | 40 | 60 |
| 50 | 0 | 100 |
| 55 | 0 | 100 |
| 60 | 95 | 5 |

Flow rate: 1 mL/min
Temperature: 35° C.
Detection: UV detection at 280 nm
Injection volume: 10 µL The cryptotanshinone standard at 0.25 g/L has an elution peak at 49 mn (FIG. 1).

Figure 2:
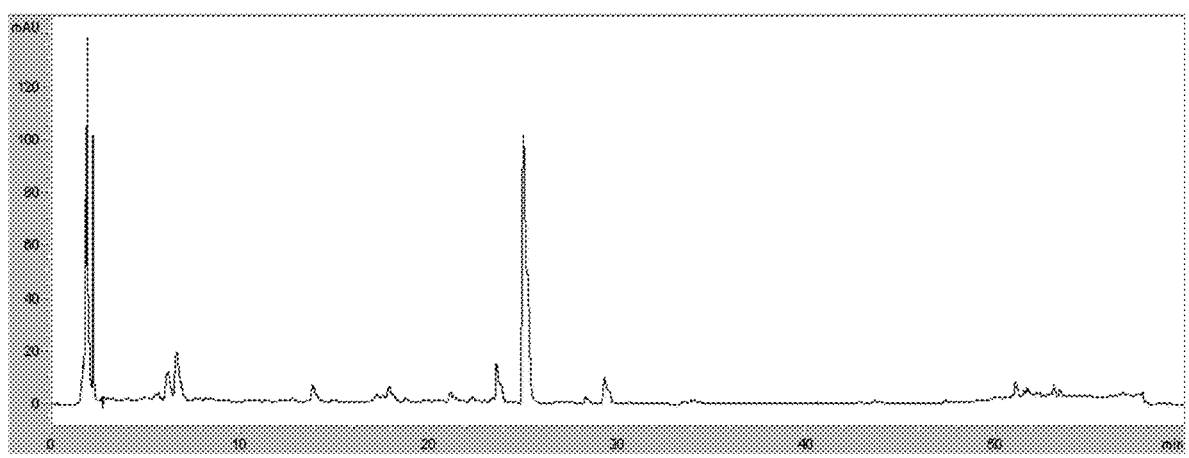
FIG. 2: the HPLC chromatogram of the extract of Example 1 according to the invention.

There is no elution peak for the extract according to the invention at the retention time of 49 mn (see FIG. 2).

The extract according to the invention contains no cryptotanshinone. The quantification limit was determined at 5 ppm.

Example 2

The extract of Example 2 is obtained by implementing the following method:
- dissolve 100 g of powdered dried *Salvia miltiorrhiza* roots in 1 L of a mixture of water/butylene glycol (water/glycol butylene ratio 20/80),
- separate the soluble and insoluble phase by decantation, recover the soluble phase,
- decolor by adding additive,
- filter with a molecular sieve to exclude the molecules with a molar mass of more than 2000 Da,
- sterilize through a 0.22µ filter.

The extract of Example 2 is in the form of a clear yellow liquid. The dry matter content is 30.0 g/L.

The chemical composition of the extract of Example 2 is as follows (the percentages being given by weight of dry matter):
Sugars: 25.2 g/L, i.e. 84%
Polyphenols: 3.3 g/L, i.e. 11%,
Ashes: 4%,
Proteins: 1%

The salvianolic acid B content is estimated at 392 ppm.

The absence of cryptotanshinone was demonstrated by means of the method described in the "*Salvia miltiorrhiza* Root" monograph of the Japanese Pharmacopeia.

This monograph describes the following method of identification:

Place 1 g of *Salvia miltiorrhiza* root compound in 10 mL of diethyl ether. Agitate for 10 mn and filter. Evaporate the filtrate and dissolve the residue in 1 mL of ethyl acetate. Use this solution as the sample. Deposit the sample on a thin-layer chromatography plate in the form of a 10 μL spot. Develop the plate of silica with a mixture of hexane and ethyl acetate (3:1) for about 10 cm. Dry the plate. Over time, a brownish-red spot with an Rf of 0.4 is observed.

Thin-layer chromatography was performed:
1/ on the *Salvia miltiorrhiza* root
2/ on a standard solution of cryptotanshinone (Sigma C5624-98%) of 2 g/L in methanol
3/ on the active ingredient according to the invention of Example 2, at different concentrations
4/ on the active ingredient according to the invention of Example 2 after filtration through a C18-Maxi-Clean™ cartridge
5/ on a standard solution of cryptotanshinone of 1 g/L after filtration through a C18-Maxi-Clean™ cartridge.

Figure 3:
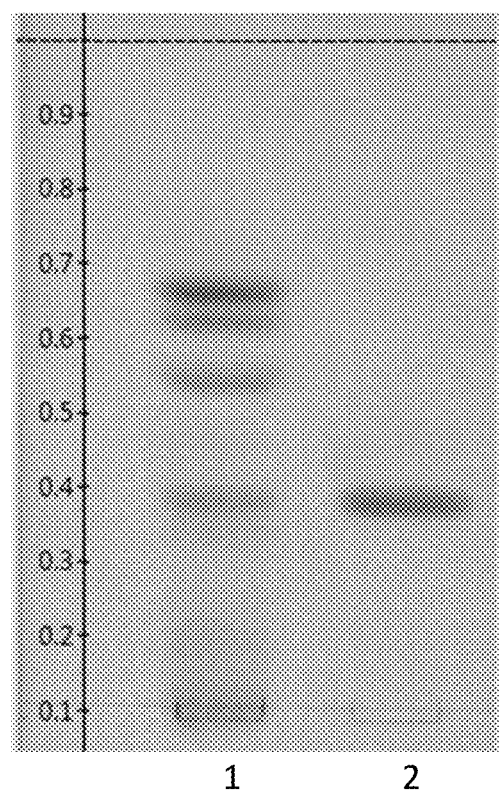
FIG. 3: is chromatography on a thin layer of *Salvia miltiorrhiza* root and of cryptotanshinone (white light), lane one is a *Salvia miltiorrhiza* root sample; lane two is cryptotanshinone 2 g/L (methanol)

Cryptotanshinone is the compound with an Rf of 0.4 under the study conditions, described by the Japanese Pharmacopeia, Sample 1, the *Salvia miltiorrhiza* root, clearly shows the presence of cryptotanshinone in the plant (FIG. 3).

Figure 4:
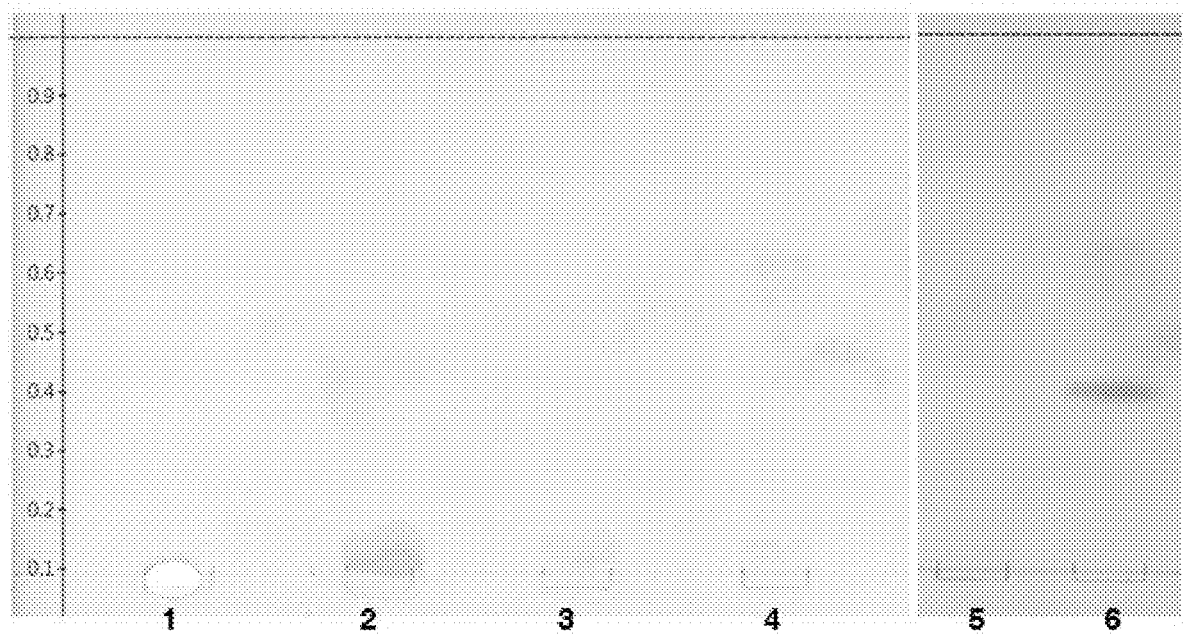
FIG. 4: is chromatography on a thin layer of an extract according to the invention and of cryptotanshinone (white light), Active ingredient according to the invention Ex 2 (10 µL spot) is in lane 1; Active ingredient according to the invention Ex 2, ¼ dilution (10 µL spot) is in lane 2; Active ingredient according to the invention Ex 2, 1/10 dilution (10 µL spot) is in lane 3; Active ingredient according to the invention Ex 2, 1/10 dilution (5 µL spot) is in lane 4; Active ingredient according to the invention Ex 2, after filtration through a C18-Maxi-Clean™ cartridge (10 µL spot) is in lane 5; and Cryptotanshinone after filtration through a C18-Maxi-Clean™ cartridge (10 µL spot) is in lane 6.

By contrast, the extract according to the invention was analyzed according to this methodology. The result is shown in FIG. 4. Profiles 1 to 4 show an interference between the solvent of the extract and the elution solvent. For this reason, a pre-filtration was performed using a C18-Maxi-Clean™ cartridge to remove the solvent of the extract before depositing (profile 5). This test was also performed on a standard solution of cryptotanshinone at 1 g/L in the same solvent (profile 6).

The molecule of cryptotanshinone is not present in the extract according to the invention (profile 5) and is always present in the standard solution (profile 6).

The extract according to the invention contains no cryptotanshinone.

Examples of Compositions

Example 3: Anti-Redness Formula Comprising an Extract of *Salvia miltiorrhiza* Roots The formulation is as follows:

| | | | |
|---|---|---|---|
| A. | Water | | qsp 100% |
| | Preservative | | 1% |
| | Glycerin | | 2% |
| | Extract of Example 1 | | 2.5% |
| B. | DUB 1632 | (Stéarinerie Dubois) | 1% |
| | Lanol 1688 | (Seppic) | 5% |
| | DUB 5545 | (Stéarinerie Dubois) | 5% |
| | Myglyol 812N | (Cremer Oleo GmbH & Co. KG) | 4% |
| | Tegosoft TN2 | (Evonik Industries AG Personal Care) | 1% |
| C. | Carbopol EDT 2020 | (Lubrizol) | 1% |
| D. | NaOH | | qsp pH = 6.1 |

This composition is a brownish, glossy, odorless emulsified gel with a soft texture.

It is easy to apply and soft, spreads smoothly, penetrates quickly, and has a soft, light finish and a filmogenic effect.

The pH of the composition is 6.1.

It is obtained by performing the following steps:
Mix A. Heat in a water-bath to 80° C. under magnetic agitation,
Mix B. Heat in a water-bath to 80° C. under magnetic agitation,
At 80° C., emulsify A in B under a rotor stator at 1800 rpm,
At 30° C., add C under a rotor stator at 1500 rpm,
Then adjust the pH, with D, still under agitation.

Example 4: Emulsified Gel Comprising an Extract of *Salvia miltiorrhiza* Roots The formulation is as follows:

| | | | |
|---|---|---|---|
| A. | Water | | qsp 100% |
| | Preservative | | 1% |
| | Extract of Example 2 | | 2.5% |
| B. | DUB SSIC | (Stéarinerie Dubois) | 2.5% |
| | DUB ININ A | (Stéarinerie Dubois) | 2.5% |
| | DUB DIS | (Stéarinerie Dubois) | 1% |
| C. | DC 200 | (Dow Corning) | 5% |
| | Sepiplus 400 | (Seppic) | 1.5% |

This composition is a white, glossy, odorless gellified emulsion with a thick texture.

It has a flexible and light hold, spreads coolly and smoothly and penetrates quite quickly, with a soft dry finish and a siliconized feel.

The composition has a pH of 5.2.

It is obtained by performing the following steps:
Mix A. Heat in a water-bath to 50° C. under magnetic agitation, so as to thoroughly homogenize the preservative.
Add B and agitate under a rotor stator at 2,000 rpm,
At 30° C., add C in the order indicated, under a rotor stator at 1,500 rpm,
Leave under agitation until completely homogenized.

Example 5: Cream-Mask Formula Comprising an Extract of *Salvia miltiorrhiza* Roots The formulation is as follows:

| | | | |
|---|---|---|---|
| A. | Water | | qsp 100% |
| | Preservative | | 1% |
| B. | DUB MM | (Stéarinerie Dubois) | 0.5% |
| | DUB Vinyl | (Stéarinerie Dubois) | 0.5% |
| | Phytowax Olive 16L55 | (Sophim) | 0.5% |
| | Montanov 14 | (Seppic) | 3% |
| | Sensanov WR | (Seppic) | 2% |
| | Miroir De Sucre | (Laboratoire Hytech) | 3% |
| | Euthanol G 16 S | (BASF) | 5% |
| C. | Sepimax ZEN | (Seppic) | 0.5 |
| | Extract of Example 1 | | 2.5 |
| D. | NaOH | | qsp pH = |

This composition is a white, glossy, odorless emulsion with a semi-thick texture.

It has a flexible application, excellent spread with a refreshing sensoriality typical of the "quick break" effect, and a fat and glossy filmogenic finish, enabling a pause time before removing the excess.

The composition has a pH of 5.9.

It is obtained by performing the following steps:
Mix A. Heat in a water-bath to 80° C. under magnetic agitation, ensuring that the preserver is thoroughly dispersed.
Mix B. Heat in a water-bath to 80° C. under magnetic agitation magnetic.
Emulsify A in B, under a rotor stator at 1,500 rpm.
As soon as homogenization is complete, add C and agitate under a rotor stator at 1,300 rpm.
At room temperature, and under agitation, adjust the pH with D.

Leave for a few minutes under a rotor stator at 1,000 rpm.

Example 6: Day Cream Formula Comprising an Extract of *Salvia miltiorrhiza* Roots The formulation is as follows:

| A. | Water |  | qsp 100% |
|---|---|---|---|
|  | Preservative |  | 1% |
|  | Extract of Example 2 |  | 2.5% |
| B. | Shea butter | (Sophim) | 2% |
|  | Peach butter | (Sophim) | 1% |
|  | DUB Dipa | (Stéarinerie Dubois) | 5% |
|  | Sophiderm | (Sophim) | 5% |
|  | Easynov | (Seppic) | 3% |
|  | Montanov L | (Seppic) | 3% |
|  | DUB CG7 | (Stéarinerie Dubois) | 2% |
|  | Cupuaçu butter | (Hytech Laboratory) | 2% |
| C. | DUB Velvet Gum | (Stéarinerie Dubois) | 4% |
|  | DC 9040 | (Dow Corning) | 4% |

This composition is a white, glossy, odorless, siliconized emulsion with a firm texture.

It has a soft application, easy spread and an evanescent effect, with a fairly rapid penetration and a soft, filmogenic finish.

The composition has a pH of 5.3.

It is obtained by performing the following steps:

Mix A. Heat in a water-bath to 80° C. under magnetic agitation.

Mix B. Heat in a water-bath to 80° C. under magnetic agitation.

Emulsify B in A, under a rotor stator at 2200 rpm.

When cold, add C and agitate under a rotor stator at 2000 rpm.

Leave under agitation until complete.

Evaluation of Cosmetic Efficacy According to the Invention

I. Capacity of an Extract According to the Invention to Inhibit TRPV1 Receptors

The aim of this study is to evaluate the capacity of an extract of *Salvia miltiorrhiza* roots to inhibit the activity of TRPV1 (Transient receptor potential vanilloid 1) receptors of human sensory neurons that play a major role in the detection and transmission of sensations of pain and itching to the central nervous system.

This study was performed on a model of human sensory neurons derived from hiPS cells (human-induced Pluripotent Stem Cells) in co-culture with human keratinocytes. The activation of TRPV1 receptors is characterized by a massive entry of calcium into the cytoplasm of the sensory neurons that can be captured by a fluorescent probe and analyzed by epifluorescence microscopy.

The operating protocol is described below:

D0, culture of sensory neurons derived from hiPS cells:

The hiPS (human-induced Pluripotent Stem) cells are seeded in a culture medium and incubated at 37° C.

D14, placed in co-culture with normal human keratinocytes:

Some human keratinocytes are seeded onto the carpet of sensory neurons. The cells are then incubated at 37° C. in an atmosphere containing 5% $CO_2$.

D19:

Pre-treatment

The co-culture of human sensory neurons/keratinocytes is or is not pre-treated with an extract according to the invention of the example at 0.25% (V/V) or with capsazepine at 10 µm (inhibitor of TRPV1).

Incubation with the Fluo-4 fluorescent probe.

The culture medium is removed and replaced with a medium containing the fluorescent probe Fluo-4 (Fluo-4 Acetoxymethyl) with or without the presence of the extract according to the invention at 0.25% (V/V) or capsazepine at 10 µm.

Treatment (activation of the TRPV1 receptors).

At the end of this incubation, the co-cultures are placed under an epifluorescence microscope. The sensory neurons are observed for three minutes, during which an image is taken every 333 ms. Five seconds after the start of recording, the neurons are simulated with capsaicin at 10 µM to activate the TRPV1 receptors. The capsaicin treatment is performed with and without the extract of Example 1 at 0.25% (V/V) or capsazepine at 10 µM.

Analysis of the activity of the TRPV1 receptors by mobilization of cytoplasmic calcium.

The activation of the TRPV1 receptors causes an entry of calcium into the sensory neurons. This entry of calcium is captured by the Fluo-4 probe, causing an increase in the level of fluorescence in the neurons. The greater the increase in the level of fluorescence, the more the TRPV1 receptors are activated.

The average of the increase in the level of fluorescence was compared in percentage terms to the non-activated control condition.

The results are given in Table 1:

TABLE 1

Capacity of an extract of *Salvia miltiorrhiza* roots to inhibit the activity of TRPV1 receptors of sensory neurons activated by capsaicin

|  | Mobilization of cytoplasmic calcium (%) | Inhibition of TRPV1 receptors/activated control neurons (%) |
|---|---|---|
| Non-activated sensory neurons | | |
| Control | 100 | |
| Sensory neurons activated by capsaicin | | |
| Control | 330♦♦♦ | |
| Capsazepine 10 µM | 131*** | 199% |
| Example according to the invention Example 1 at 0.25% | 215*** | 115% |

♦♦♦significant result according to the One-Way ANOVA test/non-activated control sensory neurons ($p < 0.001$)
***significant results according to the One Way ANOVA test/activated control sensory neurons ($p < 0.001$)

The treatment of the co-culture by capsaicin causes a significant increase in the mobilization of cytoplasmic calcium in sensory neurons.

This increase is significantly inhibited to 199% by a treatment with capsazepine showing a specific activation of the TRPV1 receptors.

Tested at 0.25%, the extract according to the invention significantly inhibits to 115% the activation of the TRPV1 receptors of the sensory neurons. It therefore limits the hyperactivity of the sensory nerve fibers of the skin.

II. Capacity of an Extract According to the Invention to Limit the Inflammatory Response in a Pollution Context II.1. Study of the Synthesis of COX-2

The purpose of this study is to evaluate the capacity of an extract of *Salvia miltiorrhiza* roots to limit the synthesis of cyclo-oxygenase 2 (COX-2) in the event of an inflammation caused by a pollutant (fine particles: PM).

Every day, sensitive skin is subjected to a multitude of external stimuli (UV radiation, atmospheric pollution, etc.) that can cause a non-specific inflammatory reaction contributing to the feeling of discomfort. In response to a stress with fine particles (PM), the keratinocytes synthesize COX-2, an enzyme playing a major role in the inflammatory process. Inhibiting the synthesis of COX2 can therefore limit the damage caused by pollution.

The expression of COX-2 has been evaluated by immunohistochemistry on SILABSKIN® REs subjected to repeated treatments with fine particles (PM) in order to mimic a polluted environment.

A. Culture and Treatments of SILABSKIN® REs

Human keratinocytes were cultivated in a specific culture medium

D0:
Normal human keratinocytes were seeded on inserts then incubated at 37° C. in an atmosphere containing 5% $CO_2$.

D2 to D13:
The culture medium was changed every 2 days.

D14 and D15, treatments of SILABSKIN® REs:
SILABSKIN® REs were treated topically with a solution of fine particles (PM), with or without the presence of the extract of Example 1 at 0.25% (V/V), or with capsazepine at 1 µm.

D16:
The SILABSKIN® REs were recovered, fixed, dehydrated and embedded in paraffin. Sections (4 µm) were then cut using a microtome (RM2125RT, Leica).

B. Analysis of the Expression of COX-2 by Immunohistochemical Marking

Removal of paraffin with xylene
Unmasking the antigenic sites
Saturation
Primary antibody: rabbit monoclonal anti-COX-2 antibody
Secondary antibody: coupled Alexa Fluor® 488 rabbit anti-IgG antibody The expression of COX-2 was proportional to the intensity of the green fluorescence present on the SILABSKIN® REs. A quantitative analysis of the images was performed with the aid of Matlab® version R2012b (MathWorks) software. The results were expressed in arbitrary units (UA). The results obtained are given in Table 2.

TABLE 2

Capacity of an extract of *Salvia miltiorrhiza* roots to limit the synthesis of COX-2 on SILABSKIN ® REs in the event of an inflammation caused by a pollutant (PM).

|  | Synthesis of COX-2 ($\times 10^3$ UA) | Synthesis of COX-2/ polluted control (%) |
|---|---|---|
| Normal SILABSKIN ® REs | | |
| Control | 265 | |
| Polluted SILABSKIN ® REs | | |
| Control | 899♦♦♦ | |
| Capsazepine 1 µM | 659* | −38 |
| Extract according to the invention Example 1 at 0.25% | 682* | −34 |

♦♦♦significant result according to the Wilcoxon Mann Withney test/SILABSKIN ® RE normal controls (p < 0.001)
*significant results according to the Wilcoxon Mann Withney test/SILABSKIN ® RE polluted controls (p < 0.05)

It will be noted that treatment with fine particles (PM) causes a significant increase in the expression of COX-2 on the SILABSKIN® REs.

This increase is significantly inhibited to 38% by a treatment with capsazepine, showing that the synthesis of COX-2 generated by the PMs is partly due to the activation of the TRPV1 receptors.

Tested at 0.25% on SILABSKIN® RE, an extract of *Salvia miltiorrhiza* roots significantly inhibits to 34% the synthesis of COX-2 caused by a treatment with fine particles (PM). It thus limits the inflammatory reaction caused by atmospheric pollution.

II.2. Study of the Secretion of PGE2

The purpose of this study is to evaluate the capacity of an extract of *Salvia miltiorrhiza* roots to limit the secretion of prostaglandins E2 (PGE2) in the event of an inflammation caused by a pollutant (fine particles: PM).

Every day, sensitive skin is subjected to a multitude of external stimuli (UV radiation, atmospheric pollution, etc.) that can cause a non-specific inflammatory reaction contributing to the feeling of discomfort. In response to a stress with fine particles (PM), the keratinocytes synthesize PGE2s, which are major mediators of inflammation. Inhibiting the synthesis of PGE2 can therefore limit the damage caused by pollution.

This study was performed by ELISA assay on the culture supernatant of human keratinocytes subjected to a treatment with fine particles (PM) mimicking a polluted environment.

The operating protocol of the study is described below.

D0:
Normal human keratinocytes were seeded in a culture medium and incubated at 37° C. in an atmosphere containing 5% $CO_2$.

D2:
Pre-treatment:
The keratinocytes were pretreated with or without the extract of Example 1 at 0.025% and 0.05% (V/V) or with capsazepine at 0.5 µM (inhibitor of TRPV1). The cells were then incubated for 30 minutes at 37° C. in an atmosphere containing 5% $CO_2$.

Treatment with fine particles (PM):
The keratinocytes were treated with a solution of particles.

The cells were then incubated for 24 hours at 37° C. in an atmosphere containing 5% $CO_2$.

D3, recovery of supernatants:
The culture supernatants were recovered and the PGE2s were assayed using an ELISA Kit (Enzo Life Sciences).

The results obtained are given in Table 3.

TABLE 3

Capacity of an extract according to the invention to limit the secretion of PGE2 by human keratinocytes in the event of an inflammation caused by a pollutant (PM).

|  | PGE2 Content (pg/mg of proteins) | PGE2 Content/PM- treated control (%) |
|---|---|---|
| Normal keratinocytes | | |
| Control | 380 | |
| Keratinocytes treated with PMs | | |
| Control | 627♦♦♦ | |
| Capsazepine 0.5 µM | 433* | −78 |
| Example according to the invention Example 1 at 0.025% | 512 | −47 |

TABLE 3-continued

Capacity of an extract according to the invention to limit
the secretion of PGE2 by human keratinocytes in the event
of an inflammation caused by a pollutant (PM).

|  | PGE2 Content (pg/mg of proteins) | PGE2 Content/PM-treated control (%) |
|---|---|---|
| Example according to the invention Example 1 at 0.050% | 392* | −95 |

♦♦♦significant result according to the Student t test/normal control keratinocytes (p < 0.01)
*significant results according to the Student t test/PM-treated control keratinocytes test (p < 0.05)

It will be noted that treatment with fine particles (PM) caused a significant increase in the secretion of PGE2 by the keratinocytes.

This increase was significantly inhibited to 78% by a treatment with capsazepine, showing that the inflammation generated by the PMs is partly due to the activation of the TRPV1 receptors of the keratinocytes.

Tested at 0.05%, an extract of *Salvia miltiorrhiza* roots significantly increased to 95% the secretion of PGE2 by the keratinocytes after a treatment with fine particles (PM). It thus greatly limits the inflammatory reaction caused by atmospheric pollution.

III. Effect of an Extract According to the Invention on the Barrier Function

The purpose of this study is to evaluate in vivo the influence of the extract of *Salvia miltiorrhiza* roots formulated at 2.5% in emulsion on the quality of the barrier function as regards the face and hands of individuals with sensitive skin.

This effect has been evaluated with the aid of the following methods:
- study of the transepidermal water loss, measured using a Tewamètre® TEW meter;
- study of the hydration rate, measured with the aid of a Cornéomètre® corneometer;
- self-evaluation of the perceived performance via a subjective evaluation questionnaire.

The formula of the composition tested on the face is as follows:

| Isononyl isononanoate (Lanol 99, Seppic) | 5.0% |
|---|---|
| Arachidyl alcohol/Behenyl Alcohol/Arachidyl glucoside (Montanov 202, Seppic) | 3.0% |
| Active ingredient according to the invention (Example 1) | 2.5% |
| Cetearyl alcohol/cetearyl glucoside (Montanov 68, Seppic) | 2.0% |
| Preservatives | 1.0% |
| Polyacrylamide/C13-14 isoparaffin/Laureth-7 (Sepigel 305, Seppic) | 0.3% |
| Water | qsp 100 |

The formula of the composition tested on the hands is as follows:

| Glycerol | 5.0% |
|---|---|
| Active ingredient according to the invention (Example 1) | 2.5% |
| PEG-7 glyceryl cocoate (DUB GC7, Dubois) | 1.2% |
| Preservatives | 1.0% |
| Caprylic/capric triglycerides (DUB MCT 5545, Dubois) | 0.8% |
| Acrylate/C10-30 alkyl acrylate crosspolymer (Carbopol ULTREZ20, Noveon) | 0.3% |
| NaOH | qsp pH 4.5 |
| Water | qsp 100 |

The studies were conducted with the parameters described below.

A. Study Relating to the Face
Panel:
20 female, Caucasian, healthy volunteers of an average age of 43±10 years having stated that they had sensitive skin according to the items on the questionnaire SS-10 (Misery et al., Acta Derm Venereol, 2014), having reacted to capsaicin during a stinging test and having a low tolerance threshold to cold (measurement via the TSA II system).
Methods of application:
Twice-daily applications
B. Study Relating to the Hands
Panel:
13 female, Caucasian, healthy volunteers of an average age of 46±11 years having stated that they had sensitive skin according to the items on the questionnaire SCC-10 (Misery et al., Acta Derm Venereol, 2014) and having a low tolerance threshold to cold as regards their hands (measurement via the TSA II system).
Methods of application:
4 applications per day (morning at 8:00, midday, afternoon at 4:00, at bedtime).

The results obtained for the different tests are presented below.

Transepidermal Water Loss:
A summary of the results corresponding to the effect of an extract of *Salvia miltiorrhiza* roots formulated at 2.5% compared to the placebo, on the transepidermal water loss of the skin measured using a Tewamètre® for the face and hands, is shown in Table 4:

TABLE 4

Effect of an extract according to the invention formulated at 2.5% on transepidermal water loss

|  | Variation/Placebo (%) |
|---|---|
| Face | −9.6 |
| Hands | −9.2 |

It was observed that after 14 days of application, an extract according to the invention formulated at 2.5% significantly reduced transepidermal water loss from the face and hands (−9.6%, $p=0.0012$ and −9.2%, $p=0.0287$ respectively) of volunteers with sensitive skin. 70% of them experienced a positive effect on the face and 69% on the hands.

Study of the Rate of Hydration
A summary of the results corresponding to the effect of an extract of *Salvia miltiorrhiza* roots formulated at 2.5% compared to the placebo, on skin hydration measured with the aid of a Cornéomètre® for the cheeks and hands, is shown in Table 5.

TABLE 5

Effect of an extract according to the invention formulated at 2.5% on the hydration rate

|  | Variation/Placebo (%) |
|---|---|
| Face | +13.3 |
| Hands | +10.3 |

It was observed that after 14 days of application, an extract according to the invention formulated at 2.5% significantly increased the hydration rate for the face and hands (+13.2%, p=0.0001 and +10.3%, p=0.0147 respectively) of volunteers with sensitive skin. 90% of them experienced a positive effect on the face and 69% on the hands.

Subjective Evaluation as Regards the Face:

The results of the closed questions are given in Table 6.

TABLE 6

Self-evaluation of an extract according to the invention formulated at 2.5% after 14 days of twice-daily applications to the face in comparison to the placebo

| | Cumulative "tend to agree" and "agree" answers (%) | |
| --- | --- | --- |
| | Placebo | Extract according to the invention 2.5% |
| Skin more resistant to external aggressions | 78 | 94 |
| Skin lastingly hydrated | 67 | 83 |

It was observed that after 14 days of application of an extract of Salvia miltiorrhiza roots, the skin was:
- more resistant to external aggressions for 94% of the volunteers against 78% for the placebo formula (significant difference, p=0.0301);
- lastingly hydrated for 83% of the volunteers against 67% with the placebo (p=0.1131).

Subjective Evaluation as Regards the Hands:

The results of the closed questions are given in Table 7.

TABLE 7

Self-evaluation of an extract of Salvia miltiorrhiza roots formulated at 2.5% after 14 days of applications to the hands in comparison to the placebo

| | Cumulative "tend to agree" and "agree" answers (%) | |
| --- | --- | --- |
| | Placebo | Extract according to the invention 2.5% |
| Hands more hydrated | 77 | 100 |
| Hands softer | 77 | 100 |
| Hands less sensitive to aggressions | 62 | 92 |
| Soothing treatment | 46 | 92 |

It was observed that after 14 days of application of an extract of Salvia miltiorrhiza roots to the hands:
- all of the volunteers observed that their hands were more hydrated and softer, against 77% for the placebo (p=0.0003 and p=0.0020 respectively);
- 92% of them said that their hands seemed less sensitive to aggressions, against only 62% for the placebo (p=0.0043);
- 92% observed that the treatment had soothing properties (p=0.0002).

IV. Effect of an Extract According to the Invention on Skin Sensitivity

The purpose of this study is to evaluate in vivo the effect of an extract of Salvia miltiorrhiza roots formulated at 2.5% in emulsion on skin sensitivity as regards the face, before and after 14 days of twice-daily applications. This study was carried out on Caucasian volunteers and Asian volunteers having a skin reactivity score of more than 3 for Asian skins and 5 for Caucasian skins, during the application of capsaicin to their nostrils.

The studies were conducted with the parameters described below.

A. Caucasian Panel:

Panel:

20 female, healthy volunteers of an average age of 43±10 years having stated that they had sensitive skin according to the items on the questionnaire SS-10 (Misery et al., Acta Derm Venereol, 2014), having reacted to capsaicin during a stinging test and having a low tolerance threshold to cold (measurement via the TSA II system).

Methods:

Study of skin reactivity after the application of capsaicin ($3.10^{-4}$%) (stinging test); and self-evaluation of the perceived performance via a subjective evaluation questionnaire.

The cosmetic formula tested on the Caucasian volunteers was as follows:

| | |
| --- | --- |
| Isononyl isononanoate (Lanol 99, Seppic) | 5.0% |
| Arachidyl alcohol/Behenyl Alcohol/Arachidyl glucoside (Montanov 202, Seppic) | 3.0% |
| Active ingredient according to the invention (Example 1) | 2.5% |
| Cetearyl alcohol/cetearyl glucoside (Montanov 68, Seppic) | 2.0% |
| Preservatives | 1.0% |
| Polyacrylamide/C13-14 isoparaffin/Laureth-7 (Sepigel 305, Seppic) | 0.3% |
| Water | qsp 100 |

B. Asian Panel

Panel:

31 female, healthy volunteers of an average age of 44±9 years having reacted to capsaicin during a stinging test and having been exposed to urban pollution for at least one year before the start of the study.

Methods:

Skin reactivity study after the application of capsaicin ($1.10^{-5}$%) (stinging test); and study of neurosensitivity (Neurometer).

The cosmetic formula tested on the Asian volunteers was as follows:

| | |
| --- | --- |
| Glycerin | 6.2% |
| Cetearyl ethylhexanoate (Lanol 1688, Seppic) | 3.0% |
| Coco-Caprylate/Caprate (DUB 810C, Dubois) | 3.0% |
| Active ingredient according to the invention (Example 1) | 2.5% |
| Isononyl isononanoate (Lanol 99, Seppic) | 2.0% |
| Preservatives | 1.0% |
| Polyacrylate Crosspolymer-6 (Sepimax zen, Seppic) | 0.5% |
| Hydroxyethyl Acrylate/Sodium Acryloyldimethyl Taurate Copolymer (Sepinov EMT 10, Seppic) | 0.5% |
| Aqua (water) | qsp 100 |

The results obtained for the different tests are presented below.

Study of Skin Reactivity

A summary of the results corresponding to the effect of an extract of Salvia miltiorrhiza roots formulated at 2.5% compared to the placebo, on skin reactivity evaluated with the aid of a stinging test, is given in Table 8 for the Caucasian panel and in Table 9 for the Asian panel.

TABLE 8

Effect of an extract according to the invention formulated at 2.5% on stinging sensations- Caucasian panel

| Score D 14-D 0 Perception of stinging | 0 mn | 1 mn | 2 mn | 5 mn |
|---|---|---|---|---|
| Placebo | 0.25 | −0.10 | −0.10 | −0.50 |
| Extract according to the invention 2.5% | −0.5* | −0.75** | −0.95** | −0.70* |

**significant difference/D 0 ($p < 0.01$)
*significant differences/D 0 ($p < 0.05$)

TABLE 9

Effect of an extract according to the invention formulated at 2.5% on stinging sensations - Asian panel

| Score D 14-D 0 Perception of stinging | 0 mn | 1 mn | 2 mn | 5 mn |
|---|---|---|---|---|
| Placebo | −0.32 | −0.55 | −0.74 | −0.52 |
| Extract according to the invention 2.5% | −1.29* | −1.16 | −1.87** | −1.39* |

**significant difference/D 0 ($p < 0.01$)
*significant differences/D 0 ($p < 0.05$)

It was observed that after 14 days of application, an extract of *Salvia miltiorrhiza* roots improved the tolerance of the skin to capsaicin in the panel of Caucasian and Asian volunteers.

In fact, an extract of *Salvia miltiorrhiza* roots formulated at 2.5% significantly limited the unpleasant sensations caused by the application of capsaicin on the nasolabial folds.

Study of the Neurosensitivity on the Neurometer® CPT

A summary of the results corresponding to the effect of an extract of *Salvia miltiorrhiza* roots formulated at 2.5% compared to the placebo, on the skin neurosensitivity evaluated with the aid of a Neurometer CPT on the Asian volunteers, is given in Table 10.

TABLE 10

Change in the current-perception threshold between D 0 and D 14 for the placebo formula and the extract according to the invention

|  | Placebo | Extract according to the invention at 2.5% |
|---|---|---|
| Neurosensitivity | 0 | −19 |

It was observed that after 14 days of application, an extract of *Salvia miltiorrhiza* roots formulated at 2.5% caused a significant reduction of 19% in skin neurosensitivity after stimulation of the nerve fibers via a 250 Hz electric current. This effect was observed in 65% of the volunteers.

Subjective Evaluation

The results of the self-evaluation carried out by the Caucasian volunteers are given in Table 11.

TABLE 11

Self-evaluation of an extract according to the invention formulated at 2.5% after 14 days of twice-daily applications to the face in comparison with the placebo

| | Cumulative "tend to agree" and "agree" answers (%) | |
|---|---|---|
| | Placebo | Extract according to the invention 2.5% |
| With this treatment my skin is less reactive | 67 | 94 |
| This treatment is dedicated to sensitive skins | 67 | 94 |

It was observed that after 14 days of application of an extract of *Salvia miltiorrhiza* roots to the face:
- 94% of the volunteers observed that their skin was less reactive against 67% for the placebo (p=0.0379);
- 94% of the subjects agreed that the treatment is dedicated to sensitive skins against 67% of volunteers having used the placebo (p=0.0169).

V. Effect of an Extract According to the Invention on the Inflammatory Component The purpose of this study was to evaluate in vivo the influence of an extract of *Salvia miltiorrhiza* roots formulated at 2.5% in emulsion on the inflammatory component of the skin before and after 28 days of twice-daily applications, in comparison to a placebo formula.

The cosmetic formula containing the extract was as follows:

| Cetearyl ethylhexanoate (Lanol 1688, Seppic) | 5.0% |
|---|---|
| Extract of *Salvia miltiorrhiza* according to the invention (Example 1) | 2.5% |
| Preservatives | 1.0% |
| Carbomer (ULTREZ10, Noveon) | 0.5% |
| NaOH | qsp pH 5 |
| Water | qsp 100 |

This effect was evaluated by using an inflammation model using leukotriene B4 (LTB4), the topical application of which causes a local inflammation of the skin promoting the recruitment of leukocyte inflammatory cells. The study of the inflammatory response of the skin as a result of this aggression was observed in vivo with the aid of a confocal laser microscope (VivaScope®).

The study was conducted on 17 female, Caucasian, healthy volunteers of an average age of 44±10 years and having a normal skin as regards the inner forearms.

A summary of the results corresponding to the score of the intensity of the inflammatory reaction given by experts based on acquisitions made in vivo by confocal laser microscopy is given in Table 12.

TABLE 12

Effect of an extract according to the invention formulated at 2.5% on the inflammatory response of the skin

| | D 0 | D 28 | Variation/D 0 (%) |
|---|---|---|---|
| Placebo | 889 | 725 | −164% |
| Extract according to the invention 2.5% | 1022 | 618 | −404% |

It was observed that, after 14 days of application, an extract of *Salvia miltiorrhiza* roots formulated at 2.5% significantly limited the local inflammatory response of the skin faced with an aggression caused by a topical application of LTB4 (−240%, p=0.0069). This effect was observed in 71% of the volunteers.

VI. Effect of an Extract According to the Invention on Skin Sensitized by Cold

The purpose of this study is to evaluate in vivo the influence of an extract of *Salvia miltiorrhiza* roots formulated at 2.5% in emulsion on the skin sensitivity caused by cold on volunteers with sensitive skin.

The formula of the composition tested on the face and that tested on the hands was identical to that of the test described in point III.

The studies were conducted with the parameters described below.

A. Study Relating to the Face

Panel:

20 female, Caucasian, healthy volunteers of an average age of 43±10 years having stated that they had sensitive skin according to the items on the questionnaire SS-10 (Misery et al., Acta Derm Venereol, 2014), having reacted to capsaicin during a stinging test and having a low tolerance threshold to cold (measurement via the TSA II system).

Methods of application:

Twice-daily applications.

Methods study of the tolerance to cold threshold measured via TSAII, as regards the face;

study of skin redness after an exposure to cold as shown in a digital photograph;

self-evaluation of the performance perceived via a subjective evaluation questionnaire.

B. Study Relating to the Hands

Panel:

13 female, Caucasian, healthy volunteers of an average age of 46±11 years having stated that they had sensitive skin according to the items on the questionnaire SCC-10 (Misery et al., Acta Derm Venereol, 2014) and having a low tolerance to cold threshold as regards their hands (measurement via the TSA II system).

Methods of application:

4 applications per day (morning at 8:00, midday, afternoon at 4:00, at bedtime).

Methods study of the tolerance to cold threshold measured via TSAII, as regards the hands;

self-evaluation of the performance perceived via a subjective evaluation questionnaire.

The results obtained for the different tests are presented below.

Study of the Tolerance to Cold Threshold

A summary of results corresponding to the effect of an extract of *Salvia miltiorrhiza* roots formulated at 2.5% compared to the placebo, on the tolerance to cold threshold measured with the aid of TSAII as regards the cheeks and hands is presented in Table 13.

TABLE 13

Effect of an extract according to the invention formulated at 2.5% on the tolerance to cold threshold

|  | Variation/Placebo (%) |
|---|---|
| Face | +7.5 |
| Hands | +15.5 |

It was observed that after 14 days of application, an extract of *Salvia miltiorrhiza* roots reduced the sensitivity to cold of subjects with sensitive skin by 3° C. on the face and 4° C. on the hands. In fact, the tolerance to cold threshold of the volunteers was significantly increased both as regards the face and the hands (+7.5%, p=0.0092 and +15.5%, p=0.0325 respectively). 70% of them experienced a positive effect on their face and 62% on their hands.

Study of Skin Redness after Exposure to Cold

A summary of the results corresponding to the immediate effect of an extract of *Salvia miltiorrhiza* roots formulated at 2.5% compared to the placebo, on parameter a* characteristic of the skin redness caused by a cold environment, is presented in Table 14.

TABLE 14

Effect of an extract according to the invention formulated at 2.5% in emulsion on the development of skin redness after a 15-minute exposure to cold.

|  | Increase in the intensity of skin redness after exposure to cold |
|---|---|
| Placebo | 7E+05 |
| Extract according to the invention 2.5% | 4E+05 |
| Variation/placebo (%) | −43% |

After a single application, an extract of *Salvia miltiorrhiza* roots formulated at 2.5% reduced skin reactivity to cold, characterized by an appearance of skin redness (−43%, p=0.0005). This effect was observed in 85% of the volunteers.

VII. Evaluation of the Effect on the Comfort and Protection of the Skin

VII.1. Subjective Evaluation by a Caucasian Panel

The purpose of this study was to evaluate in vivo the influence of an extract of *Salvia miltiorrhiza* roots formulated at 2.5% in emulsion on the quality of the skin (comfort and protection) of volunteers with sensitive skin on the face and body.

This effect was evaluated by the volunteers by conducting a self-evaluation of the perceived performance via a subjective evaluation questionnaire at the end of the study.

A. Study Relating to the Face

Panel:

20 female, Caucasian, healthy volunteers of an average age of 43±10 years having stated that they had sensitive skin according to the items on the questionnaire SS-10 (Misery et al., Acta Derm Venereol, 2014), having reacted to capsaicin during a stinging test and having a low tolerance to cold threshold (measurement via the TSA II system).

Methods of application:

Twice-Daily Applications

B. Study Relating to the Hands

Panel:

13 female, Caucasian, healthy volunteers of an average age of 46±11 years having stated that they had a sensitive skin according to the items on the questionnaire SCC-10 (Misery et al., Acta Derm Venereol, 2014) and having a low tolerance to cold threshold as regards their hands (measurement via the TSA II system).

Methods of application:

4 applications per day (morning at 8:00, midday, afternoon at 4:00, at bedtime).

The results obtained for the different tests are presented below.

Study Relating to the Face
The results of the closed questions are given in Table 15.

TABLE 15

Self-evaluation of an extract according to the invention
formulated at 2.5% after 14 days of twice-daily applications
to the face in comparison to the placebo

| | Cumulative "tend to agree" and "agree" answers (%) | |
|---|---|---|
| | Placebo | Extract according to the invention 2.5% |
| This treatment protects my skin from external aggressions | 83 | 94 |
| This treatment reduces the sensations of tightness | 61 | 83 |
| This treatment reduces skin discomfort | 67 | 94 |

It was observed that after 14 days of application of an extract according to the invention to the face:
- 94% of the volunteers found their skin to be protected from external aggressions (non-significant difference);
- the sensations of tightness were reduced for 83% of the volunteers against only 61% for the placebo (p=0.0387);
- skin discomfort was reduced by 94% amongst them against only 67% for the placebo (p=0.0169).

Study Relating to the Hands
The results of the closed questions are given in Table 16.

TABLE 16

Self-evaluation of an extract according to the invention
formulated at 2.5% after 14 days of applications
to the hands in comparison to the placebo

| | Cumulative "tend to agree" and "agree" answers (%) | |
|---|---|---|
| | Placebo | Extract according to the invention 2.5% |
| Hands protected | 62 | 92 |
| Nourishing treatment | 77 | 100 |

It was observed that after 14 days of applications of an extract according to the invention to the hands:
- 92% of the volunteers found their hands were protected, against 62% for the placebo (p=0.0023);
- all of the subjects agree that the treatment was nourishing, against 77% of volunteers having used the placebo (p<0.0001).

VII.2. Subjective Evaluation by an Asian Panel

The purpose of this consumer test was to compare the effectiveness of a treatment containing an extract of *Salvia miltiorrhiza* roots formulated at 2.5% to its placebo.

This study was conducted on 126 women living in Shanghai (China), aged between 20 and 65 (average age 37.3±9.6 years), having stated that they have skin sensitive chiefly to pollution and possibly to cold or changes in temperature and users of face treatments for sensitive skin or products claiming to have anti-pollution effects.

The volunteers were divided into 2 groups:
- extract according to the invention group: 63 women of an average age of 37±10 years;
- placebo group: 63 women of an average age of 37±10 years.

The evaluations were made at the end of the 1st day of the test as well as after 14 days of twice-daily applications with the aid of self-evaluation questionnaires.

The results obtained are given below.

Results after the First Day of Application
The results of the closed question were as follows:

TABLE 17

Perception of consumers after the first day of use of a
formula containing an extract according to the invention
formulated at 2.5% in emulsion or of a placebo formula

| | Cumulative "agree" and "totally agree" answers (%) | |
|---|---|---|
| | Placebo | Extract according to the invention 2.5% |
| My skin seems less sensitive | 77.8 | 88.9 |
| Skin discomfort is reduced | 84.1 | 92.1 |
| My skin is less itchy | 81.0 | 87.3 |

Results after 14 Days of Use
The results of the closed questions were as follows:

TABLE 18

Perception of consumers after 14 days of use of a formula
containing an extract according to the invention formulated
at 2.5% in emulsified gel or a placebo formula

| | Consumers (%) | |
|---|---|---|
| | Placebo | Extract according to the invention 2.5% |
| My skin seems lastingly hydrated | 82.5 | 88.9 |
| My skin seems more flexible | 84.1 | 85.7 |
| My skin seems nourished | 90.5 | 95.2 |
| My skin seems less sensitive | 88.9 | 92.1 |
| Skin discomfort is reduced | 95.2 | 98.4 |
| Redness is attenuated | 87.3 | 93.7 |
| My skin no longer seems irritated | 82.5 | 88.9 |
| My skin is more resistant to changes in temperature | 85.7 | 87.3 |

It was observed overall that the women who had used the formula containing an extract of *Salvia miltiorrhiza* roots attributed better results to the various items than those who tested the placebo formula: there were more women who observed an attenuation of skin redness and agreed that their skin was less sensitive and less irritable.

VIII. Study of the Effect of the Polyphenolic Fraction of an Extract of *Salvia miltiorrhiza* Roots The purpose of this study is to evaluate the effect of the polyphenolic fraction of an extract of Example 2.

100 mL of extract was treated with polyvinylpolypyrrolidone (5 g) in order to eliminate the polyphenols. The solution obtained was agitated for 2 hours at room temperature then filtered. Fraction A was thus obtained.

Fraction A and the whole extract were analyzed by ionic liquid chromatography (Dionex ICS 3000 system).

The total quantity of polyphenols in Fraction A and in the extract was determined by colorimetry.

The analysis of the phenolic compounds was performed by UPLC-UV-MS/MS.

The chromatographic analyses showed that Fraction A was purified from sugars because it contained 95% of the sugars of the extract. This fraction was purified of polyphenols, because it comprised only 11.5% of the phenolic compounds of the extract.

The test of Study II.2 on the secretion of PGE2 was performed on the extract and on Fraction A.

The results are given in Table 19.

TABLE 19

Capacity of an extract according to the invention and of Fraction A to limit the secretion of PGE2 by human keratinocytes during an inflammation caused by a pollutant (PM)

| | PGE2 Content (pg/mg of proteins) | PGE2 Content/PM-treated control (%) |
|---|---|---|
| Normal keratinocytes | | |
| Control | 400 ± 43 | |
| Keratinocytes treated with PMs | | |
| Control | 594 ± 71 | |
| Extract according to the invention of Example 2 at 0.050% | 412 ± 71 | −94 |
| Fraction A at 0.05% | 588 ± 63 | −3 |

It was observed that Fraction A has no efficacy on the PGE2s, which shows that the sugars do not confer this efficacy to the extract.

It is therefore the phenolic compounds of the active ingredient that are responsible for the efficacy of the extract on the PEG2s.

BIBLIOGRAPHY

Boillat A, Alijevic O, Kellenberger S. Calcium entry via TRPV1 but not ASICs induces neuropeptide release from sensory neurons. Mol Cell Neurosci. 2014 July; 61:13-22.

Draelos Z D. Sensitive skin: perceptions, evaluation, and treatment. Am J Contact Dermat Off J Am Contact Dermat Soc. 1997 June; 8(2):67-78.

Duarte I, Silveira J E P S, Hafner M de F S, Toyota R, Pedroso D M M. Sensitive skin: review of an ascending concept. An Bras Dermatol. 2017; 92(4):521-5.

Gouin O, L'Herondelle K, Lebonvallet N, Le Gall-Ianotto C, Sakka M, Buhé V, et al. TRPV1 and TRPA1 in cutaneous neurogenic and chronic inflammation: pro-inflammatory response induced by their activation and their sensitization. Protein Cell. 2017 Mar. 31;

Misery L, Loser K, Ständer S. Sensitive skin. J Eur Acad Dermatol Venereol JEADV. 2016 February; 30 Suppl 1:2-8.

Pinto P, Rosado C, Parreirão C, Rodrigues L M. Is there any barrier impairment in sensitive skin?: a quantitative analysis of sensitive skin by mathematical modeling of transepidermal water loss desorption curves. Skin Res Technol Off J Int Soc Bioeng Skin ISBS Int Soc Digit Imaging Skin ISDIS Int Soc Skin Imaging ISSI. 2011 May; 17(2):181-5.

Richters R, Falcone D, Uzunbajakava N, Verkruysse W, van Erp P, van de Kerkhof P. What is sensitive skin? A systematic literature review of objective measurements. Skin Pharmacol Physiol. 2015; 28(2):75-83.

Richters R J H, Falcone D, Uzunbajakava N E, Varghese B, Caspers P J, Puppels G J, et al. Sensitive Skin: Assessment of the Skin Barrier Using Confocal Raman Microspectroscopy. Skin Pharmacol Physiol. 2017; 30(1):1-12.

Saint-Martory C, Roguedas-Contios A M, Sibaud V, Degouy A, Schmitt A M, Misery L. Sensitive skin is not limited to the face. Br J Dermatol. 2008 January; 158(1):130-3.

Tóth B I, Oláh A, Szöllősi A G, Bíró T. TRP channels in the skin. Br J Pharmacol. 2014 May; 171(10):2568-81.

Vestergaard C, Hvid M, Johansen C, Kemp K, Deleuran B, Deleuran M. Inflammation-induced alterations in the skin barrier function: implications in atopic dermatitis. Chem Immunol Allergy. 2012; 96:77-80.

What is claimed is:

1. A method of treating sensitive skin, the method consisting of the step of: applying topically to the sensitive skin an effective amount of an extract of *Salvia miltiorrhiza* roots, wherein the extract is obtained by extracting *Salvia miltiorrhiza* roots with a water/butylene glycol mixture and wherein the extract does not contain molecules with a molecular mass exceeding 2000 Da.

2. The method of claim 1, wherein the skin has been exposed to cold and/or pollution and/or a chemical stress.

3. The method of claim 1, wherein the application of the *Salvia miltiorrhiza* root extract neutralizes the neuronal hyperactivity of the skin, and/or preserves the barrier function of the skin, and/or limits the inflammation of the skin.

4. The method of claim 1, wherein the application of the *Salvia miltiorrhiza* root extract reduces cutaneous hypersensitive reactions and/or reduces sensation of the skin tightening.

5. The method of claim 1, wherein the extract of *Salvia miltiorrhiza* root comprises at least 5% by weight of polyphenols in relation to the total weight of dry matter of the extract.

6. A cosmetic method of treatment of the skin, the method consisting of topically applying onto the skin a cosmetic composition comprising at least 0.25% by total weight of an extract of *Salvia miltiorrhiza* root comprising at least 5% by weight of polyphenols in relation to the total weight of dry matter of the extract;

wherein the extract further comprises butylene glycol and water, and thereby soothing the skin, wherein the extract is obtained by extracting *Salvia miltiorrhiza* roots with a water/butylene glycol mixture, and wherein the extract does not contain molecules with a molecular mass exceeding 2000 Da.

7. The cosmetic method of treatment of claim 6, wherein the skin is sensitive skin.

8. The cosmetic method of treatment of claim 6, wherein the skin has been exposed to cold and/or pollution and/or a chemical stress.

* * * * *